United States Patent [19]

Yamanaka et al.

[11] 4,308,273
[45] Dec. 29, 1981

[54] 1,6-NAPHTHYRIDINE DERIVATIVES, AND ANTIDINIC AND CEREBRAL CIRCULATION IMPROVER CONTAINING SUCH DERIVATIVES

[75] Inventors: Hiroshi Yamanaka; Takao Sakamoto, both of Sendai; Akira Shiozawa, Tokyo; Yuh-Ichiro Ichikawa, Chiba; Michio Ishikawa, Tokyo; Hiroshi Miyazaki, Kawasaki, all of Japan

[73] Assignee: Nippon Kayaku Kabushiki Kaisha, Tokyo, Japan

[21] Appl. No.: 83,556

[22] Filed: Oct. 10, 1979

[30] Foreign Application Priority Data

Oct. 17, 1978 [JP] Japan .............................. 53-126780

[51] Int. Cl.$^3$ .................. A61K 31/435; C07D 471/04
[52] U.S. Cl. ............................ 424/256; 542/434; 542/469; 546/122
[58] Field of Search ................ 546/122; 542/469, 434; 424/256

[56] References Cited

PUBLICATIONS

Chemical Abstracts vol. 67 (1967) Item 32611Z, abstracting Haglid "Ark. KEMI," vol. 26, No. 41, pp. 489–495 (1967).

Primary Examiner—Robert T. Bond
Attorney, Agent, or Firm—Wegner & Bretschneider

[57] ABSTRACT

This invention relates to the novel 1,6-naphthyridine derivatives useful as antidinic and/or cerebral circulation improver, such novel derivatives being represented by the following general formula:

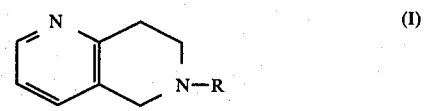

(I)

(wherein R is a $C_{2-10}$ alkyl which may have hydroxyl, lower alkylcarbonyl, lower alkyloxycarbonyl or phenoxy as a substituent; a $C_{2-10}$ unsaturated aliphatic hydrocarbon group having unsaturated double bond(s); a phenyl-lower alkyl which may have halogen, lower alkyl, lower alkoxy or lower alkylthio as substituent(s) attached to the phenyl ring; a cinnamyl which may have halogen, nitro, lower alkyl or lower alkoxy as substituent(s) attached to the phenyl ring; propargyl; 1-naphthylmethyl; 2-thenyl; cyclohexenyl; a cycloalkyl-lower alkyl with a 3- to 6-membered ring; ½($C_{2-4}$ alkylene); ½(butenylene), or diphenylmethyl, and in case two alkoxyl groups are present attached to the phenyl ring, they may be bonded to form a ring) and salt thereof.

12 Claims, No Drawings

1,6-NAPHTHYRIDINE DERIVATIVES, AND ANTIDINIC AND CEREBRAL CIRCULATION IMPROVER CONTAINING SUCH DERIVATIVES

BACKGROUND OF THE INVENTION

Owing to the diversification of the social life accompanied with the rapid development of the material civilization, there are reported every year an increasing number of patients suffering from vertigo or dizziness. Because the pathogenesis of vertigo is diversified, a variety of drugs, such as vasodilators, antihistaminics, tranquilizers and vitamines are used. These drugs are prescribed to the patient according to his complaint and symptoms. None of these drugs, however, can be a fundamental therapy for vertigo. Recently, new antidinic drugs such as betahistine and diphenidol are used for treatment vertigo or dizziness. Nevertheless, they still have much to be improved in that betahistine is short-acting and that diphenidol has a hallusinogenic action. Thus, anti-vertigo drugs with much higher selectivity to vertigo and longer duration of action should be developed urgently.

From this point of view, the present inventors have searched an anti-vertigo drug acting selectivity on the vestibular function which plays an important role in the cause of vertigo. Spontaneous nystagmus by unilateral destruction of the labyrinth was taken as an index for estimating the anti-vertigo drugs. As a result of a series of studies, it was found that the naphthyridine derivatives represented by the above-shown general formula (I) inhibited markedly the nystagmus and showed much more selectivity, longer duration of action and lower toxicity. These derivatives are also quite novel in chemical structure.

A further study on the pharmacological effect of said compounds revealed a noticeable and selective cerebral vasodilating action. Drugs used at present for the therapy of cerebrovascular disease are mainly vasodilators, including anticoagulants, thrombolytics. Nevertheless, there is no drug that acts selectively on cerebral vasculature and many of these drugs cause postural hypotension. Furthermore, there is no convincing evidence that these drugs are practically useful for patients with cerebrovascular disease. The compounds of the present invention may be of value in improving cerebrovascular disease in view of the fact that they increased markedly the vertebral arterial flow while causing only very weak hypotensive and tachycardiac effects.

The present invention was attained on the basis of these findings.

SUMMARY OF THE INVENTION

This invention relates to the novel 1,6-naphthyridine derivatives represented by the following general formula:

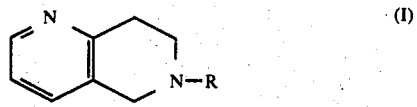
(I)

(wherein R is a $C_{2-10}$ alkyl which may have hydroxyl, lower alkylcarbonyl, lower alkyloxycarbonyl or phenoxy as a substituent; a $C_{2-10}$ unsaturated aliphatic hydrocarbon group having unsaturated double bond(s); a phenyl-lower alkyl which may have halogen, lower alkyl, lower alkoxy or lower alkylthio as substituent(s) attached to the phenyl ring; a cinnamyl which may have halogen, nitro, lower alkyl or lower alkoxy as substituent(s) attached to the phenyl ring; propargyl; 1-naphthylmethyl; 2-thenyl; cyclohexenyl; a cycloalkyl-lower alkyl with a 3- or 6-membered ring; ½($C_{2-4}$ alkylene); ½(butenylene), or diphenylmethyl, and in case two alkoxyl groups are present attached to the phenyl ring, they may be bonded to form a ring) and salt thereof, a process for preparing such derivatives, and an antidinic and/or cerebral circulation improver containing such derivatives as active principle.

The compounds of the above-shown general formula (I) can be prepared by first reacting 1,6-naphthyridine with a compound of the formula:

(wherein R is as defined above, and X is a halogen or aryl sulfoxy) To obtain a quaternary salt of 1,6-naphthyridine of the formula:

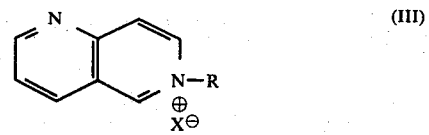

and then reducing such quaternary salt.

Each group of R is specified as follows. The $C_{2-10}$ alkyl group may be either straight chain or branched, for example, ethyl, n-propyl, isopropyl, n-butyl, isobutyl, n-amyl, isoamyl, 2-methylbutyl, n-hexyl, isohexyl, 2-ethylbutyl, 2,3-dimethylbutyl, n-heptyl, isoheptyl, n-octyl, isooctyl, n-nonyl, isononyl and n-decyl, etc. Such alkyl group may have a substituent such as hydroxyl, lower alkylcarbonyl (for example $C_{1-4}$ alkylcarbonyl such as methylcarbonyl, ethylcarbonyl, propylcarbonyl or butylcarbony), lower alkyloxycarbonyl (for example $C_{1-4}$ alkyloxy carbonyl such as methyloxycarbonyl, ethyloxycarbonyl, propyloxycarbonyl or butyloxycarbonyl) or phenoxy.

The $C_{2-10}$ unsaturated aliphatic hydrocarbon group may have one or two unsaturated double bonds and may be either straight chain or branched. Examples of such group are vinyl, propenyl, butenyl, pentenyl, hexenyl, heptenyl, octenyl, nonenyl, 3,7-dimethyl-octa-2,6-dienyl, etc.

The phenyl-lower alkyl, in which the alkyl group has 1 to 6 carbon atoms, is for example benzyl, phenylethyl, phenylpropyl, phenylbutyl, phenylpentyl, phenylhexyl, etc. The alkyl of these groups may be branched and the phenyl of these groups may have one or more substituents. The substituent is, for example, a halogen (such as chloro, bromo or fluoro), a lower alkyl (for example $C_{1-6}$ alkyl such as methyl, ethyl, propyl, butyl, pentyl or hexyl), a lower alkoxy (for example $C_{1-6}$ alkoxy such as methoxy, ethoxy, butoxy, heptoxy or hexyloxy) or a lower alkylthio (for example $C_{1-3}$ alkylthio such as methylthio, ethylthio or propylthio). In case such substituent are two alkoxy groups, they may be bonded together to form a ring.

The cinnamyl group may have one or more substituents substituted to the phenyl ring. Such substituent is a halogen (such as chloro, bromo or fluoro), a nitro, a lower alkyl (for example $C_{1-4}$ alkyl such as methyl, ethyl, propyl or butyl), or a lower alkoxy (for example $C_{1-4}$ alkoxy such as methoxy, ethoxy, propoxy or butoxy). There may exist two or more substituents, and in case such substituent is two alkoxyl groups, they may be linked together to form a ring.

The 3- to 6-membered ring cycloalkyl-lower alkyls are, for example, cyclopropylmethyl, cyclopropylethyl, cyclopropylpropyl, cyclobutylmethyl, cyclobutylethyl, cycloheptylmethyl and cyclohexylmethyl.

The term "½($C_{2-4}$ alkylene)" indicates that the 6-position of two 5,6,7,8-tetrahydro-1,6-naphthyridine are bonded to both ends of a $C_{2-4}$ alkylene such as ethylene, trimethylene or tetramethylene. The compound having this group is, for example, 1,3-bis[6-(5,6,7,8-tetrahydro-1,6-naphthyridino)] propane.

The term "½(butenylene)" means that the 6-position of two 5,6,7,8-tetrahydro-1,6-naphthyridine are bonded to both ends of butenylene.

X represents halogen such as chloro, bromo or iodo, or arylsulfonyloxy such as tosyl.

The term "lower" (for "lower alkyl", "lower alkoxy", etc.) used in this specification means that the carbon number in such alkyl, alkoxy, etc., is 1 to 6, unless otherwise specified.

The antidinic and/or cerebral circulation improver according to this invention comprise 1 to 99% by weight of a 1,6-naphthyridine derivative of the general formula (I) and 99 to 1% by weight of an adjuvant (or adjuvants).

The 1,6naphthyridine derivatives of the general formula (I) according to this invention are usually prepared into a form suited for use and an effective dose thereof is administered to man or animal to improve the cerebral circulation and/or to prevent dizziness or vertigo.

DETAILED DESCRIPTION OF THE INVENTION:

Typical examples of the compounds provided according to this invention are listed in the following table.

TABLE 1

Derivatives of 5,6,7,8-tetrahydro-1,6-naphthyidiné 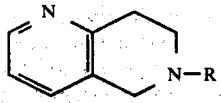

| Compound No. | R | bp (°C./mmHg) or mp* | MS m/e(rel. intensity: |
|---|---|---|---|
| 1 | $C_2H_5$ | 97°/1.2 | 162 ($M^+$, 728), 161(100) |
| 2 | n-$C_3H_7$ | 85–86°/0.55 | 176($M^+$, 3.3), 147(100) |
| 3 | i-$C_3H_7$ | 85–94°/0.7 | 176($M^+$, 5.1), 175(3.1), 161(100), 133(8.3), 118(11.6) |
| 4 | n-$C_4H_9$ | 106–116°/1.2 | 190($M^+$, 61.9), 189(35.2), 133(61.5), 118(100), 105(69.1) |
| 5 | i-$C_4H_9$ | 86–95°/0.7 | 190($M^+$, 3.9), 147(100), 118(20.9) |
| 6 | n-$C_5H_{11}$ | 119°/0.9 | 204($M^+$, 10.8), 175(20.6), 161(35.3), 147(100), 118(24.1) |
| 7 | i-$C_5H_{11}$ | 112°/0.7 | 204($M^+$, 11.7), 147(100), 133(12.6), 120(18.8), 118(45.0) |
| 8 | n-$C_6H_{13}$ | 115–117°/0.5 | 218($M^+$, 9.4), 148(14.6), 147(100) |
| 9 | n-$C_7H_{15}$ | 126–128°/0.5 | 232($M^+$, 4.3), 147(100) |
| 10 | n-$C_8H_{17}$ | 144–145°/0.7 | 246($M^+$, 100), 245(42.7), 147(21.9), 120(36.9), 118(25.9) |
| 11 | n-$C_{10}H_{21}$ | 156–160°/0.4 | 274($M^+$, 25.3), 273(12.5), 147(100) |
| 12 | $CH_2CH{=}CH_2$ | 98°/1.0 | 174($M^+$, 38.1), 173(100), 147(59.7) |
| 13 | $CH_2CH{=}CHCH_3$ | 105–106°/0.7 | 188($M^+$, 37.6), 187(60.7), 173(18.2), 147(31.4), 134(89.4), 133(100), 118(38.0) |
| 14 | $CH_2CH_2CH{=}CH_2$ | 100–103°/0.9 | 188($M^+$, 1.6), 147(100) |
| 15 | $CH_2CH_2CH_2CH{=}CH_2$ | 110–112°/0.35 | 202($M^+$, 5.2), 201(5.2), 147(100), 118(15.8) |
| 16 | $CH_2CH{=}C(CH_3)_2$ | 123°/1.0 | 202($M^+$, 27.8), 201(15.9), 187(16.7), 159(28.1), 133(100), 118(39.7) |
| 17 | $CH_2CH_2C(CH_3){=}CH_2$ | 110°/0.6 | 202($M^+$, 0.71), 147(100) |
| 18 | $CH_2CH{=}CH{-}n{-}C_3H_7$ | 126–128°/0.8 | 216($M^+$, 100), 215(25.6), 159(31.5), 133(83.3) |
| 19 | $CH_2CH{=}CH{-}n{-}C_5H_{11}$ | 128–133°/0.4 | 244($M^+$, 31.9), 243(55.8), 229(60.0), 187(49.6) |
| 20 | geranyl | 159–160°/0.4 | 270($M^+$, 12.9), 269(8.5), 201(39.3), 147(56.8), 133(100) |
| 21 | $CH_2C{\equiv}CH$ | 105–106°/0.7 | 172($M^+$, 69.2), 171(100), 133(63.1), 106(49.6), 105(93.6), 104(91.1) |
| 22 | $CH_2{-}\triangleleft$ | 104–106°/0.6 | 188($M^+$, 100), 187(92.1), 147(11.6) |
| 23 | $CH_2{-}\square$ | 122–123°/0.8 | 202($M^+$, 5.6), 147(100) |
| 24 | $CH_2{-}\pentagon$ | 139–140°/0.35 | 230($M^+$, 2.5), 147(100) |
| 25 | (cyclohexenyl) | 134–136°/0.5 | 214($M^+$, 18.8), 186(100), 171(65.4), 133(30.6), 118(32.8), 106(16.2), 81(24.0) |
| 26 | $CH_2CH_2CH_2OH$ | 120°/0.9 | 192($M^+$, 6.8), 147(100), 133(15,8), 118(20.8), 106(17.1) |
| 27 | $CH_2CH_2CH_2OC_6H_5$ | 173°/0.4 | 268($M^+$, 100), 147(100), 133(32.9), 188(13.8), 77(18.2), 65(22.3) |
| 28 | $CH_2CH_2CH_2COOC_2H_5$ | 146–148°/0.6 | 248($M^+$, 0.85), 203(8.5), 147(100), 133(66.0), 118(20.5) |

TABLE 1-continued

Derivatives of 5,6,7,8-tetrahydro-1,6-naphthyidine

| Compound No. | R | bp (°C./mmHg) or mp* | MS m/e(rel. intensity: |
|---|---|---|---|
| 29 | CH$_2$CH$_2$CH$_2$CH$_2$—C(=O)—CH$_3$ | 157–158°/0.6 | 232(M$^+$,1.3), 147(100), 133(11.3), 118(13.3) |
| 30 | CH$_2$CH$_2$CH$_2$CH$_2$CH(OH)CH$_3$ | *90.5–92.0° | 234(M$^+$, 2.6), 147(100), 133(9.6) |
| 31 | CH$_2$C$_6$H$_5$ | 156°/1.2 | 224(M$^+$, 23.8), 223(22.7), 147(15.1), 133(46.4), 91(100), 65(34.1) |
| 32 | CH$_2$C$_6$H$_4$—2-Cl | 160–162°/0.4 | 260(M$^+$+2, 25.4), 259(M$^+$+1, 36.7), 258(66.7) 133(46.1), 127(32,9) 125(100) |
| 33 | CH$_2$C$_6$H$_4$—4-Cl | 170–172°/0.7 | 260(M$^+$+2, 19.4), 259(M$^+$+1, 40.6), 258(M$^+$, 75.8), 257(58.3), 133(71.2), 127(35.8), 125(100) |
| 34 | CH$_2$C$_6$H$_4$—4-CH$_3$ | 166°/2.0 | 238(M$^+$, 10.4), 237(11.7), 133(59.1), 105(100) |
| 35 | CH$_2$C$_6$H$_4$—4-C$_2$H$_5$ | 163°/0.7 | 252(M$^+$, 46.0), 251(35.0), 147(22.3), 133(98.5), 119(100), 91(54.4) |
| 36 | CH$_2$C$_6$H$_4$—3-i-C$_3$H$_7$ | 173–175°/0.8 | 266(M$^+$, 16.4), 265(11.7), 147(12.3), 134(16.3), 133(100), 92(14.5), 91(15.0) |
| 37 | CH$_2$C$_6$H$_4$—4-i-C$_3$H$_7$ | *71–73° | 266(M$^+$, 5.4), 134(13.9), 133(100), 118(10.4), 92(11.7), 91(11.1) |
| 38 | CH$_2$C$_6$H$_4$—4-t-C$_4$H$_9$ | *61–64° | 280(M$^+$, 42.4), 147(59.1), 133(100), 118(21.2), |
| 39 | CH$_2$C$_6$H$_4$—3-OCH$_3$ | 170–172°/0.8 | 254(M$^+$, 6.9), 147(20.7), 133(100), 122(53.1) 121(33.5) |
| 40 | CH$_2$C$_6$H$_4$—4-OCH$_3$ | 182°/1.2 | 254(M$^+$, 5.4), 133(17.5), 121(100), 78(30.9), 77(34.4) |
| 41 | CH$_2$C$_6$H$_4$—4-OC$_2$H$_5$ | 172°/0.45 | 268(M$^+$, 100), 2.67(60.3), 107(6.4) |
| 42 | CH$_2$C$_6$H$_4$—4-O—N-C$_4$H$_9$ | 178°/0.25 | 296(M$^+$, 7.6), 163(28.2), 133(18.1), 118(10.3), 107(100) |
| 43 | CH$_2$C$_6$H$_4$—4-SCH$_3$ | 191–193°/0.3 | 270(M$^+$, 37.8), 269(14.5), 147(11.3), 137(100) 133(33.8), 122(17.7) |
| 44 | CH$_2$C$_6$H$_3$—3,4-di-Cl | 233–235° (HCl Salt) | 294(M$^+$+2, 4.7), 293(M$^+$+1,10.7), 292(M$^+$, 13.1), 163(13.4), 161(52.0), 159(100), 133(47.4) |
| 45 | CH$_2$C$_6$H$_3$—3,4-OCH$_2$O— | 184–185°/0.7 | 268(M$^+$, 2.6), 135(100), 133(44.7) |
| 46 | CH$_2$C$_6$H$_3$—3,4-di-OCH$_3$ | *76–77° | 284(M$^+$, 9.3), 152(81.4), 151(100), 133(57.4) |
| 47 | CH$_2$C$_6$H$_3$—3,5-di-OCH$_3$ | 191–192°/0.6 | 284(M$^+$, 2.5), 152(100), 133(18.8) |
| 48 | CH$_2$C$_6$H$_3$—3-OCH$_3$—4-OC$_2$H$_5$ | *104–105° | 298(M$^+$, 4.4), 166(73.5), 165(52.2), 137(100), 133(44.8) |
| 49 | CH$_2$C$_6$H$_3$—3-O—n-C$_3$H$_7$—4-OCH$_3$ | 194°/0.4 | 312(M$^+$, 6.7), 180(100), 179(71.8), 138(45.4), 137(67.0), 133(58.6) |
| 50 | CH$_2$C$_6$H$_3$—3,4-di-O—n-C$_3$H$_7$ | 176°/<0.001 | 340(M$^+$, 6.0), 208(100), 165(47.3), 133(52.4), 123(82.3) |
| 51 | CH$_2$C$_6$H$_3$—3,4-di-O—n-C$_4$H$_9$ | 186°/0.001 | 368(M$^+$, 5.0), 236(100), 180(31.0), 179(36.2), 133(37.3), 124(39.7), 123(84.6) |
| 52 | CH$_2$C$_6$H$_2$—3,4,5-tri-OCH$_3$ | *75–76° | 314(M$^+$, 2.2), 182(100), 167(22.5), 151(34.6), 133(21.2) |
| 53 | CH(CH$_3$)C$_6$H$_5$ | 145°/1.5 | 238(M$^+$, 18.8), 223(100), 161(20.9), 133(21.7), 105(27.3), 77(16.4) |
| 54 | CH(C$_2$H$_5$)C$_6$H$_5$ | 131–135°/0.3 | 252(M$^+$, 2.2), 224(22.5), 223(100), 118(13.5), 91(56.9) |
| 55 | CH$_2$CH$_2$C$_6$H$_5$ | 174–178°/1.3–1.4 | 238(M$^+$, 9.4), 237(8.3), 148(97.6), 118(100), 106(55.3), 91(81.9), 65(45.3) |
| 56 | CH(CH$_3$)CH$_2$C$_6$H$_5$ | 171°/0.9 | 252(M$^+$, 2.6), 162(13.9), 161(100), 118(24.8), 91(37.8) |
| 57 | CH$_2$CH$_2$CH$_2$C$_6$H$_5$ | 166–168°/0.4 | 252(M$^+$, 12.5), 147(100), 91(13.7) |
| 58 | CH$_2$CH=CH—C$_6$H$_5$ | 98°/10 | 250(M$^+$, 21.4), 159(100), 146(11.9), 133(30.4), 117(83.6), 91(45.9) |
| 59 | CH$_2$CH=CH—C$_6$H$_4$—3-F | 182–183°/1.0 | 268(M$^+$, 13.5), 267(14.9), 159(98.0), 135(77.7), 133(100) |
| 60 | CH$_2$CH—CH—C$_6$H$_4$—4-F | *86–87° | 268(M$^+$, 17.2), 267(11.5), 159(100), 135(95.3), 133(55.9) |
| 61 | CH$_2$CH=CH—C$_6$H$_4$—2-Cl | 180°/1.0 | 286(M$^+$+2, 3.7), 284(M$^+$, 11.5), 159(100), 153(9.7), 151(27.7), 133(26.7) |
| 62 | CH$_2$CH=CH—C$_6$H$_4$—3-Cl | 202–205°/1.0 | 286(M$^+$+2, 3.0), 284(9.8), 159(100), 153(11.6), 151(32.9), 133(49.4) |
| 63 | CH$_2$CH=CH—C$_6$H$_4$—4-Cl | 180°/0.08 | 286(M$^+$+2, 3.7), 284(M$^+$, 11.0), 159(100), 153(9.8), 151(34.6), 133(22.5) |
| 64 | CH$_2$CH=CH—C$_6$H$_4$—3-CH$_3$ | 183–185°/0.6 | 264(M$^+$, 17.5), 159(100), 147(21.1), 133((56.4), 131(68.4) |
| 65 | CH$_2$CH=CH—C$_6$H$_4$—4-CH$_3$ | 178°/0.4 | 264(M$^+$, 12.7), 159(100), 147(10.3), 146(15.7), 133(20.0), 131(55.7) |
| 66 | CH$_2$CH=CH—C$_6$H$_4$—4-OCH$_3$ | 200°/1.0 | 280(M$^+$, 18.7), 159(100), 148(47.7), 147(66.9) |
| 67 | CH$_2$CH=CH—C$_6$H$_4$—2-NO$_2$ | *115–116° | 295(M$^+$, 13.4), 278(34.0), 161(20.3), 147(66.4), 146(100), 133(28.4) |
| 68 | CH$_2$CH=CH—C$_6$H$_4$—3-NO$_2$ | *94–96° | 295(M$^+$, 30.9), 294(31.5), 278(26.2), 159(100), 147(31.6), 133(36.4) |
| 69 | CH$_2$CH=CH—C$_6$H$_4$—4-NO$_2$ | *146–147° | 295(M$^+$, 57.5), 159(100), 147(30.4), 146(21.9), 133(44.2) |

TABLE 1-continued

Derivatives of 5,6,7,8-tetrahydro-1,6-naphthyidine 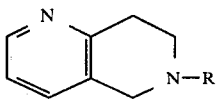

| Compound No. | R | bp (°C./mmHg) or mp* | MS m/e(rel. intensity: |
|---|---|---|---|
| 70 | CH$_2$CH=CH—C$_6$H$_4$—2,4-di-Cl | 185°/0.015 | 320(M$^+$+2, 5.1), 318(M°, 7.4), 189(2.8), 187(10.6), 185(18.5), 159(100), 133(19.4) |
| 71 | CH$_2$CH=CH—C$_6$H$_4$—3,4-di-Cl | *84–85.5° | 320(M$^+$+2, 13.6), 318(M$^+$, 19.6), 189(3.4), 187(13.9), 185(22.1), 159(100), 133(62.4) |
| 72 | CH$_2$CH=CH—C$_6$H$_4$—2,5-di-CH$_3$ | 180–181°/0.4 | 278(M$^+$, 8.7), 159(100), 145(95.7), 115(94.3) |
| 73 | CH$_2$CH=CH—C$_6$H$_4$—3,4—OCH$_2$O— | *94.5–95.5° | 294(M$^+$, 13.4), 162(30.0), 161(19.4), 147(14.9), 146(21.6), 133(27.3), 131(82.8) |
| 74 | CH$_2$CH=CH—C$_6$H$_4$—3,4-di-OCH$_3$ | 180–200°/0.001 | 310(M$^+$, 8.4), 178(50.0), 159(100), 147(95.3), 133(48.9) |
| 75 | CH(C$_6$H$_5$)$_2$ | *133–134° | 300(M$^+$, 7.5), 167(100), 165(49.6), 152(17.5), 133(24.4) |
| 76 | 2-thenyl | 165–166°/1.2 | 230(M$^+$, 17.9), 229(17.0), 133(73.0), 118(10.4), 98(12.1), 97(100) |
| 77 | 1-naphthylmethyl | *110–113° | 274(M$^+$, 80.2), 273(38.0), 133(100) |
| 78 | (CH$_2$CH$_2$CH$_2$)$_{\frac{1}{2}}$ | 210°/0.05 | 308(M$^+$, 1.4), 176(62.6), 175(23.4), 174(76.6), 173(100), 118(28.0) |
| 79 | (CH$_2$CH=CHCH$_2$)$_{\frac{1}{2}}$ | *139–141° | 320(M$^+$, 100), 186(17.8), 147(53.2), 134(42.3), 133(59.9) |

These compounds can be formed into pharmaceutically acceptable acid addition salts, for example, those prepared by use of an inorganic acid such as hydrochloric acid, sulfuric acid, phosphoric acid, etc., or an organic acid such as maleic acid, fumaric acid, malonic acid, tartaric acid, citric acid, etc. In those of the 1,6-naphthyridine derivatives of this invention which contain at least one asymmetric carbon atom in the molecule, for example, compound numbers 53, 54 and 56, there exist theoretically two optical isomers. In such case, both racemate and optical isomers are embraced in the products of this invention. The optically active compound can be obtained from the racemate by a known method, for example, the salt was prepared with an optically active acid. The produced two diastereomer salts was separated and then followed by isolation of the optical isomer from each diastereomer salt.

The prefered compounds of this invention are of the general formula (I) where R is C$_{5-7}$ alkyl, allyl, 3-butenyl, 2-octenyl, cyclopropylmethyl, cyclobutylmethyl, 3-phenoxypropyl, benzyl, 4-methylbenzyl, 3-isopropylbenzyl, 4-isopropylbenzyl, 3,4-dichlorobenzyl, 3,4-dimethoxybenzyl, 3-n-propoxy-4-methoxybenzyl, 3,4-di-n-propoxybenzyl, 2-phenylethyl or 3-phenylpropyl, cinnamyl, 2,4-dichlorocinnamyl. More preferably, allyl, 3-butenyl, 2-octenyl, cyclopropylmethyl, 3-phenoxypropyl, 4-isopropylbenzyl, 4-methylthiobenzyl or 3,4-dimethoxybenzyl, 2,4-dichlorocinnamyl.

The compounds of the formula (I) where R is allyl or cyclopropylmethyl show the most excellent antidinic activity. When the R is 3,4-dimethoxybenzyl, 4-methylthiobenzyl or 2,4-dichlorocinnamyl, the compounds produce the most salient effect for improving the cerebral circulation.

The compounds of this invention, as compared with Betahistine which is a conventional anti-vertigo drug, are exceedingly low in hypotensive action at the dose which can inhibit the nystagmus. These compounds are also weak in central action. Since these compounds also show an excellent effect for improving the cerebral circulation, they are credited with high potency as an excellent anti-vertigo drug and/or an agent improving cerebral circulation.

The compounds represented by the general formula (I) can be produced from a process shown by the following reaction formula (A):

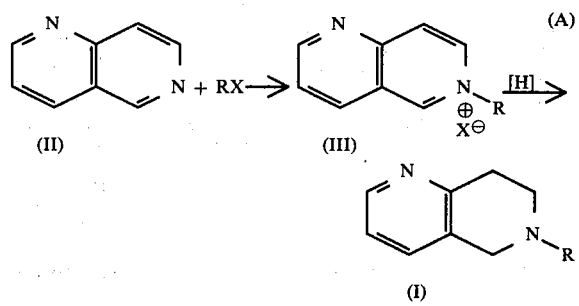

(wherein R and X are as defined above).

The 1,6-naphthyridine used as starting material in the above reaction is a known compound which can be produced, for example, by the Skraup reaction of 4-aminopyridine according to the method by W. W. Paudler et al. (T. J. Kress and W. W. Paudler: Chem. Commun. 3, 1967). The halogen compound represented by the general formula (II), may be selected from the following compounds: ethyl bromide, n-propyl bromide, isopropyl bromide, n-butyl bromide, isobutyl bromide, n-amyl bromide, isoamyl bromide, n-hexyl bromiade, n-heptyl bromide, n-octyl bromide, n-nonyl bromide, n-decyl bromide, allyl bromide, crotyl bromide, 3-butenyl bromide, isoprenyl bromide, 2-hexenyl bromide, 2-octenyl bromide, geranyl bromide, propargyl bromide, cyclopropylmethyl bromide, cyclobutylmethyl bromide, cyclohexylmethyl bromide, 2-cyclohexenyl bromide, 3-hydroxypropyl bromide, 3-phenoxypropyl bromide, 3-carbethoxypropyl bromide, 5-ethylenedioxyhexyl bromide, 5-hydroxyhexyl bromide, benzyl chloride, 2-chlorobenzyl chloride, 4-chlorobenzyl chloride, 4-methylbenzyl chloride, 4-ethylbenzyl chloride, 3-isopropylbenzyl chloride, 4-isopropylbenzyl chloride, 4-t-buthylbenzyl chloride, 3-methoxybenzyl chloride, 4-methoxybenzyl chloride, 4-ethoxybenzyl chloride, 4-n-butoxybenzyl chloride, 4-methylthiobenzyl chloride, 3,4-dichlorobenzyl chloride, 3,4-methylenedioxybenzyl chloride, 3,4-dimethoxybenzyl chloride, 3,5-dimethoxybenzyl chloride, 3-methoxy-4-ethoxybenzyl chloride, 3-n-propoxy-4-methoxybenzyl chloride, 3,4-dibutoxybenzyl chloride, 3,4,5-trimethoxybenzyl chloride, 1-phenylethyl chloride, 1-phenyl-1-propyl bromide, 2-phenylethyl bromide, 1-phenyl-2-propyl bromide, 3-phenylpropyl bromide, cinnamyl bromide, 3-fluorocinnamyl bromide, 4-fluorocinnamyl bromide, 2-chlorocinnamyl bromide, 3-chlorocinnamyl bromide, 4-chlorocinnamyl bromide, 3-methylcinnamyl bromide, 4-methylcinnamyl bromide, 4-methoxycinnamyl bromide, 2-nitrocinnamyl bromide, 3-nitrocinnamyl bromide, 4-nitrocinnamyl bromide, 2,4-dichlorocinnamyl bromide, 3,4-dichlorocinnamyl bromide, 2,5-dimethylcinnamyl bromide, 3,4-methylenedioxycinnamyl bromide, 3,4-dimethoxycinnamyl bromide, diphenylmethyl bromide, 2-thenyl chloride, 1-naphthylmethyl chloride, 1,3-dibromopropane, 1,4-dibromo-2-butene, etc. Examples of the arylsulfoxy compound are 4-pentenyl tosylate, 3-methyl-3-butenyl tosylate, etc.

For preparing a compound of this invention from the above-shown reaction formula (A), first one equivalent of 1,6-naphthyridine is mixed with more than 0.5 equivalents, preferably 1.0 to 3.0 equivalents, more preferably 1.0 to 1.5 equivalents of a halogen compound or arylsulfoxy compound represented by the general formula (II), and is reacted at a temperature within the range of 0° C. to 100° C. without using any solvent, or is reacted in an inert solvent, for example, a lower alkylnitrile such as acetonitrile or propionitrile, a ketone such as acetone or methyl ethyl ketone, a lower alcohol such as methanol or ethanol, or a lower ether such as diethyl ether, tetrahydrofuran or dioxane at a temperature of 0° C. to 100° C., to produce a quaternary salt of 1,6-naphthyridine represented by the general formula (III). This quaternary salt may or may not be isolated and is used for reduction. The reduction is generally accomplished by use of the reducing agents such as an alkaline metal aluminum hydride or an alkaline metal borohydride or by catalytic reduction, usually use of an alkaline metal borohydride is preferred as it provides a good yield. For example, in case of using sodium borohydride as the reducing agent, it is desirable to carry out the reaction in aqueous lower alcohols such as technical grade methanol, aqueous methanol, technical grade ethanol or aqueous ethanol under ice cooling or at room temperature. For isolating the desirable material of the general formula (I) from the reaction mixture, first the solvent is evaporated in vacuo and suitable quantity of water is added and the reaction product was extracted with a non-hydrophilic organic solvent such as ether, benzene, chloroform or ethyl acetate. The extract is dried and evaporated in vacuo. The resulting residue is immediately subjected to vacuum distillation, or purified by a usual purification method such as column chromatography and then distilled in vacuo. In case the product is crystallized, it may be purified by recrystallization from a suitable solvent.

The process for preparing the compounds of this invention is now described in detail by way of the following examples.

EXAMPLE 1

Preparation of 5,6,7,8-tetrahydro-6-n-amyl-1,6-naphthyridine (Compound No. 6): A mixture of 1,6-naphthyridine (6.5 g, 0.05 mol) and n-amyl bromide (9.1 g, 0.06 mol) was heated at 80°–90° C. for 28 hours. The solidified quaternary salt was dissolved in technical grade methanol (300 ml) and sodium borohydride (18.9 g, 0.5 mol) was added portionwise under ice cooling. After stirring overnight at room temperature, the reaction mixture was evaporated in vacuo, water added and extracted with benzene. The benzene layer was dried over anhydrous potassium carbonate and evaporated in vacuo. The residue was purified by alumina column chromatography (eluted successively with n-hexane, benzene and benzene-ethyl acetate (10:1)) and distilled, bp 119° C./0.9 mmHg, to afford Compound No. 6 (6.90 g, 67.6%) as a colorless oil.

IR $\nu_{max}^{neat}$ cm$^{-1}$: 2930, 2810, 1580, 1450.

NMR $\delta$(CDCl$_3$): 0.59–1.96 (6H, m; —CH$_2$CH$_2$CH$_2$CH$_2$CH$_3$); 0.93 (3H, t, J=5.5 Hz; —CH$_2$CH$_3$); 2.34–3.26 (6H, m, C$_7$—H and CH$_8$—H; =NCH$_2$CH$_2$CH$_2$—); 3.61 (2H, s, C$_5$—H); 6.99 (1H, dd, J$_{32}$=5.0 Hz, J$_{34}$=8.5 Hz; C$_3$—H); 7.30 (1H, dd, J$_{42}$=2.0 Hz, J$_{43}$=8.5 Hz; C$_4$—H); 8.33 (1H, dd, J$_{23}$=5.0 Hz, J$_{24}$=2.0 Hz; C$_2$—H).

Mass (m/e) (rel. intensity): 204 (M$^+$, 10.8), 175(20.6), 161(35.3), 147(100), 118(24.1).

EXAMPLE 2

Preparation of 5,6,7,8-tetrahydro-6-allyl-1,6-naphthyridine (Compound No. 12)

A solution of 1,6-naphthyridine (6.5 g, 0.05 mol) and allyl bromide (9.1 g, 0.075 mol) in acetone (50 ml) was refluxed for 8 hours. The precipitated quaternary salt was separated by filtration, dissolved in technical grade methanol (300 ml) and sodium borohydride (18.9 g, 0.5 mol) was added portionwise under ice cooling. After stirring overnight at room temperature, the reaction mixture was evaporated in vacuo, water added and extracted with benzene. The benzene layer was dried over anhydrous potassium carbonate and evaporated in vacuo. The residue was purified by alumina column chromatography (eluted successively with n-hexane and benzene-chloroform (3:1)) and distilled, bp 98° C./1.0 mmHg, to afford the Compound No. 12 (5.70 g, 65.5%) as a colorless oil.

IR $\nu_{max}^{neat}$ cm$^{-1}$: 2950, 2800, 1645, 1580, 1450.

NMR $\delta$(CDCl$_3$): 2.67–3.09 (4H, m; C$_7$—H and C$_8$—H); 3.19 (2H, d, J=6.0 Hz; =NCH$_2$CH=); 3.62 (2H, s; C$_5$—H); 5.00–5.47 (2H, m; —CH=CH$_2$); 5.63–6.30 (1H, m; —CH$_2$CH=CH$_2$); 6.98 (1H, dd, J$_{32}$=5.0 Hz, J$_{34}$=8.0 Hz; C$_3$—H); 7.27 (1H, dd, J$_{42}$=2.0 Hz, J$_{43}$=8.0 Hz; C$_4$—H); 8.36 (1H, dd, J$_{23}$=5.0 Hz, J$_{24}$=2.0 Hz; C$_2$—H).

Mass (m/e) (rel. intensity): 174(M$^+$, 38.1), 173(100), 147(59.7).

EXAMPLE 3

Preparation of 5,6,7,8-tetrahydro-6-(3-butenyl)-1,6-naphthyridine (Compound No. 14)

A mixture of 1,6-naphthyridine (3.9 g, 0.03 mol) and 4-bromo-1-butene (4.9 g, 0.036 mol) was heated at 70°–80° C. for 5 hours. The reaction mixture was washed with a small quantity of ether, dissolved in methanol (200 ml) and water (60 ml). To the mixture, sodium borohydride (5.7 g, 0.15 mol) was added portionwise over the internal temperature range 0° to 20° C. After stirring overnight at room temperature, the mixture was evaporated in vacuo, water added and extracted with benzene. The benzene layer was dried over anhydrous potassium carbonate and evaporated in vacuo. The resulting residue was purified by alumina column chromatography (eluted successively with petroleum ether, benzene and chloroform) and distilled, bp. 100°-103° C./0.9 mmHg, to afford the Compound No. 14 (1.6 g, 28.4%) as a colorless oil.

IR $\nu_{max}^{neat}$ cm$^{-1}$: 2925, 2800, 1640, 1575, 1450.
NMR δ(CDCl$_3$): 2.02-2.78 (4H, m; =NCH$_2$CH$_2$CH=); 2.78-3.32 (4H, m; C$_7$—H and C$_8$—H); 3.62 (2H, s; C$_5$—H); 4.83-5.30 (2H, m; —CH=CH$_2$); 5.52-6.28 (1H, m; —CH$_2$CH=CH$_2$); 6.97 (1H, dd, J$_{32}$=5.0 Hz, J$_{34}$=8.0 Hz, C$_3$—H); 7.27 (1H, dd, J$_{42}$=2.0 Hz; J$_{43}$=8.0 Hz, C$_4$—H); 8.34 (1H, dd, J$_{23}$=5.0 Hz, J$_{24}$=2.0 Hz, C$_3$—H).

Mass m/e (rel. intensity): 188(M$^+$, 116), 147(100).

EXAMPLE 4

Preparation of 5,6,7,8-tetrahydro-6-(4-pentenyl)-1,6-naphthyridine (Compound No. 15)

A mixture of 1,6-naphthyridine (6.5 g, 0.05 mol) and 4-pentenyl tosylate was heated at 80° C. for 6 hours. The reaction mixture was dissolved in methanol (300 ml) and water (100 ml). To the mixture, sodium borohydride (9.5 g, 0.25 mol) was added portionwise over the internal temperature range 0° to 20° C. After stirring overnight at room temperature, the reaction mixture was evaporated in vacuo, water added and extracted with ether. The organic layer was dried over anhydrous potassium carbonate and evaporated in vacuo. The resulting residue was purified by alumina column chromatography (eluted successively with petroleum ether and ether) and distilled, bp. 110°-112° C./0.35 mmHg, to afford the Compound No. 15 (6.9 g, 68.6%) as a colorless oil.

IR $\nu_{max}^{neat}$ cm$^{-1}$: 2925, 1640, 1575, 1450.
NMR δ(CDCl$_3$): 1.38-2.40 (4H, m; —CH$_2$CH$_2$CH$_2$CH=CH$_2$); 2.57 (2H, t, J=7.0 Hz; =NCH$_2$CH$_2$CH$_2$—); 2.67-3.27 (4H, m, C$_7$—H and C$_8$—H); 3.64 (2H, s; C$_5$—H); 4.82-5.30 (2H, m; —CH=CH$_2$); 5.53-6.28 (1H, m, —CH$_2$CH=CH$_2$); 7.00 (1H, dd, J$_{32}$=5.0 Hz, J$_{34}$=8.0 Hz; C$_3$—H); 7.31 (1H, dd, J$_{42}$=2.0 Hz, J$_{43}$=8.0 Hz; C$_4$—H); 8.37 (1H, dd, J$_{23}$=5.0 Hz, J$_{24}$=2.0 Hz; C$_2$—H).

Mass m/e (rel. intensity): 202(M$^+$, 5.2), 201(5.2), 147(100), 118(15.8).

EXAMPLE 5

Preparation of 5,6,7,8-tetrahydro-6-(5-hexanonyl)-1,6-naphthyridine (Compound No. 29)

A solution of 1,6-naphthyridine (13.0 g, 0.1 mol) and 6-bromohexan-2-one ethylene ketal (26.8 g, 0.12 mol) in acetonitrile (100 ml) was refluxed for 10 hours. The reaction mixture was evaporated in vacuo, dissolved in methanol (600 ml) and water (200 ml). To the mixture, sodium borohydride (19.5 g, 0.5 mol) was added portionwise over the internal temperature range 0° to 20° C. After stirring overnight at room temperature, the reaction mixture was evaporated in vacuo, water added and extracted with ethyl acetate. The organic layer was dried over anhydrous potassium carbonate, evaporated in vacuo. The resulting residue was dissolved in 1 N-HCl and stirred overnight, neutralized with 33% NaOH solution and extracted with chloroform. The organic layer was dried over anhydrous potassium carbonate, evaporated in vacuo. The residue was purified by alumina column chromatography (eluted with chloroform-methanol (10:1)) and distilled, bp. 157°-158° C./0.6 mmHg, to afford the Compound No. 29 (9.3 g, 40.1%) as a light yellow oil.

IR $\nu_{max}^{neat}$ cm$^{-1}$: 2925, 2800, 2760, 1707, 1576, 1450.
NMR δ(CDCl$_3$): 1.30-2.97 (4H, m; =NCH$_2$CH$_2$CH$_2$CH$_2$—); 2.15 (3H, s;

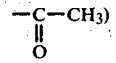

2.30-2.77 (4H, m,

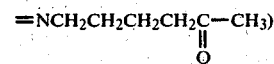

2.77-3.28 (4H, m, C$_7$—H and C$_8$—H); 3.62 (2H, s; C$_5$—H); 7.00 (1H, dd, J$_{32}$=4.5 Hz, J$_{34}$=8.0 Hz; C$_3$—H); 7.29 (1H, dd, J$_{42}$=2.0 Hz, J$_{43}$=8.0 Hz; C$_4$—H); 8.35 (1H, dd, J$_{23}$=4.5 Hz, J$_{24}$=2.0 Hz).

Mass m/e (rel. intensity): 232(M$^+$, 1.3), 147(100), 133(11.3), 118(13.3).

EXAMPLE 6

Preparation of 5,6,7,8-tetrahydro-6-(3,4-dimethoxybenzyl)-1,6-naphthyridine (Compound No. 46)

A solution of 1,6-naphthyridine (5.2 g, 0.04 mol) and 3,4-dimethoxybenzyl chloride (8.95 g, 0.048 mol) was refluxed for 3 hours. The precipitated quaternary salt was separated by filtration, dissolved in technical grade methanol (400 ml) and sodium borohydride (15.1 g, 0.4 mol) was added portionwise under ice cooling. After stirring overnight at room temperature, the reaction mixture was evaporated in vacuo, water added and extracted with chloroform. The organic layer was dried over anhydrous sodium sulfate and evaporated in vacuo. The residue was purified by alumina column chromatography (eluted successively with n-hexane, benzene and chloroform). The resulting residue was recrystallized from ether-n-hexane to afford the Compound No. 46 (6.5 g, 57.2%) as colorless prisms, mp. 76°-77° C.

IR $\nu_{max}^{KBr}$ cm$^{-1}$: 2945, 2845, 1590, 1515, 1450;
NMR δ(CDCl$_3$): 2.66-3.10 (4H, m; C$_7$—H and C$_8$—H); 3.53 (4H, s; C$_5$—H and

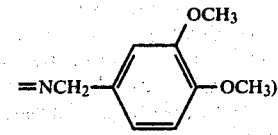

3.77 (6H, s; —OCH$_3$×2); 6.75-7.20 (5H, m; C$_3$—H, C$_4$—H and

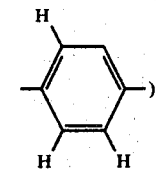

8.32 (1H, dd, J$_{23}$=4.5 Hz, J$_{24}$=1.8 Hz; C$_2$—H).

Mass (m/e) (rel. intensity): 284(M+, 9.3), 152(81.4), 151(100), 133(57.4).

EXAMPLE 7

Preparation of
5,6,7,8-tetrahydro-6-cinnamyl-1,6-naphthyridine
(Compound No. 58)

A solution of 1,6-naphthyridine (13.0 g, 0.1 mol) and cinnamyl bromide (23.6 g, 0.12 mol) in acetonitrile (100 ml) was stirred overnight at room temperature. The precipitated crystals were separated by filtration and washed with a small quantity of ether. The quaternary salt was dissolved in methanol (600 ml) and water (200 ml), and sodium borohydride (18.9 g, 0.5 mol) added portionwise over the internal temperature range 0° to 20° C. After stirring overnight at room temperature, the reaction mixture was evaporated in vacuo, water added and extracted with ether. The organic layer was dried over anhydrous potassium carbonate and evaporated in vacuo. The residue was distilled (bp. 175° C./0.4 mmHg, yellow oil; 190 g) and recrystallized from isopropyl ether to the Compound No. 58 (16.4 g, 65.6%) as a light yellow prisms, mp. 65°–66° C.

IR $\nu_{max}^{Nujoil}$ cm$^{-1}$: 1590, 1570, 1493, 1450, 1442.

NMR $\delta$(CDCl$_3$): 2.68–3.23 (4H, m, C$_7$—H and C$_8$—H); 3.30 (2H, d, J=5.5 Hz; =NC$\underline{H}_2$CH=CHC$_6$H$_5$); 3.65 (2H, s, C$_5$—H); 6.20 (1H, dd, J=5.5 Hz, J=15.5 Hz; =NCH$_2$C$\underline{H}$=CHC$_6$H$_5$); 6.63 (1H, d, J=15.5 Hz, =NCH$_2$CH=C$\underline{H}$C$_6$H$_5$); 6.97 (1H, dd, J$_{32}$=5.0 Hz, J$_{34}$=8.0 Hz; C$_3$—H); 7.11–7.57 (6H, m, C$_4$—H and —C$_6$H$_5$); 8.35 (1H, dd, J$_{23}$=5.0 Hz, J$_{24}$=2.0 Hz).

Mass m/e (rel. intensity): 250 (M+, 21.4), 159(100), 146(11.9), 133(30.4), 117(83.6), 91(45.9).

The compounds shown in the following Table 2, and 1,3-bis{6(5,6,7,8-tetrahydro-1,6-naphthyridino)}-propane(Compound No. 78) and 1,4-bis{6(5,6,7,8-tetrahydro-1,6-naphthyridino)}2-butene(Compound No. 79) were synthesized in the same way as Example 1, 2, 3, 5, 6 or 7. The compound, 5,6,7,8-tetrahydro-6-(3-methyl-3-butenyl)-1,6-naphthyridine(Compound No. 17) was synthesized in the same way as Example 4.

TABLE 2

| Compound No. | R |
|---|---|
| 1 | ethyl |
| 2 | n-propyl |
| 3 | isopropyl |
| 4 | n-butyl |
| 5 | isobutyl |
| 7 | isoamyl |
| 8 | n-hexyl |
| 9 | n-heptyl |
| 10 | n-octyl |
| 11 | n-decyl |
| 12 | crotyl |
| 16 | isoprenyl |
| 18 | 2-hexenyl |
| 19 | 2-octenyl |
| 20 | geranyl |
| 21 | propagyl |
| 22 | cyclopropylmethyl |
| 23 | cyclobutylmethyl |
| 24 | cyclohexylmethyl |
| 25 | 2-cyclohexenyl |
| 26 | 3-hydroxypropyl |
| 27 | 3-phenoxypropyl |
| 28 | 3-ethylcarbethoxypropyl |
| 29 | 5-hexanonyl |
| 30 | 5-hydroxyhexyl |
| 31 | benzyl |
| 32 | 2-chlorobenzyl |
| 33 | 4-chlorobenzyl |

TABLE 2-continued

| Compound No. | R |
|---|---|
| 34 | 4-methylbenzyl |
| 35 | 4-ethylbenzyl |
| 36 | 3-isopropylbenzyl |
| 37 | 4-isopropylbenzyl |
| 38 | 4-t-butylbenzyl |
| 39 | 3-methoxybenzyl |
| 40 | 4-methoxybenzyl |
| 41 | 4-ethoxybenzyl |
| 42 | 4-n-buthoxybenzyl |
| 43 | 4-methylthiobenzyl |
| 44 | 3,4-dichlorobenzyl |
| 45 | 3,4-methylenedioxy |
| 47 | 3,5-dimethoxybenzyl |
| 48 | 3-methoxy-4-ethoxy |
| 49 | 3-n-propoxy-4-methoxy |
| 50 | 3,4-di-n-propoxy |
| 51 | 3,4-di-n-butoxy |
| 52 | 3,4,5-trimethoxybenzyl |
| 53 | 1-phenylethyl |
| 54 | 1-phenylpropyl |
| 55 | 2-phenylethyl |
| 56 | 1-methyl-2-phenylethyl |
| 57 | 3-phenylpropyl |
| 59 | 3-fluorocinnamyl |
| 60 | 4-fluorocinnamyl |
| 61 | 2-chlorocinnamyl |
| 62 | 3-chlorocinnamyl |
| 63 | 4-chlorocinnamyl |
| 64 | 3-methylcinnamyl |
| 65 | 4-methylcinnamyl |
| 66 | 4-methoxycinnamyl |
| 67 | 2-nitrocinnamyl |
| 68 | 3-nitrocinnamyl |
| 69 | 4-nitrocinnamyl |
| 70 | 2,4-dichlorocinnamyl |
| 71 | 3,4-dichlorocinnamyl |
| 72 | 2,5-dimethylcinnamyl |
| 73 | 3,4-methylenedioxycinnamyl |
| 74 | 3,4-dimethoxycinnamyl |
| 75 | diphenylmethyl |
| 76 | 2-thenyl |
| 77 | 1-naphthylmethyl |

The antidinic and/or cerebral circulation improver provided according to this invention usually contains 1 to 99% by weight of a compound of the general formula (I) and 99 to 1% by weight of a medicinal adjuvant(s) and is used in various forms of medicinal preparations such as liquid, tablets, grains, etc.

The adjuvant used in the compositions of this invention may be of the type generally used for medicinal preparations such as excipient, binder, sweetening, disintegrator, etc.

In case of producing the tablets for example, 5 mg of a suitable compound of this invention, for example, 5,6,7,8-tetrahydro-6-cyclopropyl-1,6-naphtyridine hydrochloride is dissolved in methanol and adsorbed in 30 mg of synthetic aluminum silicate and dried. Then the mixture is added with 50 mg of Avicel 101 ® and 114 mg of potato starch, mixed sufficiently, added with 1 mg of magnesium stearate, lightly mixed and then compressed tablet to 200 mg per tablet, using 9.5 mm diameter punches.

For administering a compound of this invention to man or animal, the compound is usually worked into a suitable form of use such as above mentioned and an effective dose thereof (preferably 3–100 mg/kg per administration and 9–300 mg/kg per day) is given to man or animal orally or by other means such as injection.

The following pharmacological methods are used for assaying the pharmacological action of the compounds of the general formula (I).

(A) Anti-vertigo action (1) It is well known that vertigo resulting from the disturbance of the peripheral labyrinth is accompanied by nystagmus. So, we acutely produced the spontaneous nystagmus by unilateral destruction of the labyrinth in cats and used it as an experimental model of vertigo. a pair of Ag—AgCl cup electrodes was placed laterally to both orbits and an indifferent electrode on the forehead. The nystagmus was recorded through an amplifier. The inhibitory effect of the compounds on the nystagmus was expressed by $$\left(\frac{A-B}{A} \times 100\right),$$

where A is the frequency of the nystagmus in ten seconds before administration of the compounds and B is the frequency of the nystagmus at the maximum inhibitory point after administration. The duration of the effect was also measured. Compounds dissolved in saline were injected into the femoral vein. Betahistine and diphenidol were used as standard drugs.

(2) In order to compare adverse effects of the compounds with that of diphenidol, the effect of the compounds on the hexobarbital-induced sleeping time was examined. Groups consisted of 10 male-mice were administered the compounds or saline subcutaneously 15 min. prior to an intraperitoneal injection of sodium hexobarbital. Sleeping time for each animal in a group was measured. The averaged value of sleeping time in each group was calculated. The action of the sleeping time was expressed by the percentage of the sleeping time in the compound-treated groups to that in the saline-treated group.

(3) Acute toxicity

Values of 50% lethal dose (LD$_{50}$) of the compounds by intraperitoneal injection were estimated in male mice. The results are shown in Table 3.

TABLE 3

|  | Pharmacological evaluation (1) | | | Pharmacological evaluation (2) | Pharmacological evaluation (3) |
| --- | --- | --- | --- | --- | --- |
|  | A mg/kg | B % | C min | D % | E mg/kg |
| betahistine | 6 | 55 | 5 |  | 864 |
|  | 12 | 80 | 8 |  |  |
| diphenidol | 6 | 70 | 45 | 253.7 | 105 |
| Compounds of the invention |  |  |  |  |  |
| (6) | 12 | 86 | 10 |  | 165.3 |
| (7) | 12 | 85 | 6 |  | 219.3 |
| (8) | 12 | 88 | 10 |  | 194.5 |
| (9) | 12 | 79 | 10 |  | 208.0 |
| (12) | 6 | 90 | 40 |  | 207.5 |
|  |  |  |  | 132.5 |  |
|  | 12 | 98 | 50 |  |  |
| (14) | 12 | 77 | 28 |  | 239.0 |
| (19) | 12 | 65 | 25 |  | 304.0 |
| (22) | 6 | 85 | 19 |  | 176.0 |
|  |  |  |  | 114.4 |  |
|  | 12 | 98 | 35 |  |  |
| (23) | 12 | 83 | 8 |  | 214.0 |
| (27) | 12 | 90 | 30 |  | 208.0 |
| (31) | 12 | 57 | 9 |  | 262.1 |
| (55) | 12 | 92 | 5 |  | 219.0 |
| (57) | 12 | 97 | 10 |  | 158.8 |
| (58) | 12 | 53 | 35 |  | 263.0 |

A: Doses of compounds injected intravenously.
B: Effect of compounds on the nystagmus expressed as inhibitory percentage.
C: Duration of the effect of compounds
D: Sleeping time of the compound (50 mg/kg, subcutaneously)-treated groups expressd as percentage to that of the control group.
E: LD$_{50}$ values when injected intraperitoneally to mice.

As shown in Table 3, the compounds of the present invention were found to have a potent and long-acting anti-vertigo action while producing lower central action. Thus, they would be expected to be of great value in treatment of vertigo respectively. The results are shown in Table 4.

(3) Acute toxicity

LD$_{50}$ values of the compounds by intraperitoneal injection in mice were determined. The results are shown in Table 4.

TABLE 4

| Compounds | | Pharmacological evaluation (1) | Pharmacological evaluation (2) | | | Acute toxicity |
| --- | --- | --- | --- | --- | --- | --- |
|  |  | A % increase | B Δ mmHg | C Δ beats/min | D % increase | E mg/kg |
| Control compound | Betahistine | 90 | −100.0 | +52 | 14.3 | 864 |
| Compounds of the invention | 8 | 67 | −18.5 | +8 | 20.1 | 194.5 |
|  | 9 | 78 | −20.0 | +8 | 15.5 | 208.0 |
|  | 11 | 99 | −5.0 | +8 | 25.0 | 156 |
|  | 20 | 69 | −11.7 | +12 | 20.0 | 292 |
|  | 31 | 90 | −12.0 | +16 | 36.0 |  |
|  | 33 | 75 | −23.5 | +8 | 30.0 |  |
|  | 34 | 93 | −10.0 | +8 | 18.0 | 518 |
|  | 35 | 56 | −21.7 | +8 | 27.3 |  |
|  | 36 | 100 | −20.0 | +8 | 22.0 | 368 |
|  | 37 | 110 | −13.3 |  | 33.3 | 300 |
|  | 38 | 78 | −11.7 |  | 28.6 |  |
|  | 44 | 107 | −16.7 | +32 | 30.8 | 270 |
|  | 46 | 99 | −27.2 | +32 | 50.0 | 262 |
|  | 49 | 93 | −11.6 | +24 | 21.2 | 174 |
|  | 50 | 79 | −10.0 | +16 | 30.6 | 200 |
|  | 51 | 77 | 0 | 0 | 16.7 |  |
|  | 58 | 81 | −13.3 | +40 | 22.2 |  |
|  | 61 | 84 | −20.0 | +24 | 29.2 |  |
|  | 67 | 75 | −31.7 | +16 | 40.0 |  |
|  | 70 | 158 | −11.7 | +16 | 60.0 | 220 |
|  | 71 | 116 | −38.3 | +40 | 44.4 | 199 |

TABLE 4-continued

| Compounds | Pharmacological evaluation (1) A % increase | Pharmacological evaluation (2) | | | Acute toxicity E mg/kg |
|---|---|---|---|---|---|
| | | B Δ mmHg | C Δ beats/min | D % increase | |
| 72 | 92 | −38.3 | +48 | 40.0 | 242 |

A: Percent increase in vertebral arterial flow when injected intra-arterially (1 mg) to dogs.
B: Changes in systemic blood pressure when injected intravenously (1 mg/kg) to dogs.
C: Changes in heart rate when injected intravenously (1 mg/kg) to dogs.
D: Percent increase in vertebral arterial flow when injected intravenously (1 mg/kg) to dogs.
E: $LD_{50}$ values when injected intraperitoneally to mice.

From these results, it was found that the compounds of the present invention acted directly on the vertebral vasculature and increased the blood flow at the doses that affect hardly systemic blood pressure and heart rate. Thus, they may be of great value in the treatment of cerebrovascular disease.

(B) Cerebral vasodilating action (1) For the experimental evaluation of cerebral vasodilating action, the canine vertebral arterial preparation was used. The carotid arterial blood was led to the vertebral artery by a short extracorporeal loop. The vertebral arterial flow was measured by an electromagnetic flow transducer inserted in the circuit. The action of the compounds on the vertebral arterial flow was expressed by percent increase when 1 mg of each compound was injected intra-arterially. Their results are shown in Table 4.

(2) In order to confirm the pharmacological effect of the above compounds by systemic administration, effects of intravenous injection of 1 mg/kg of the compounds on mean arterial pressure, heart rate and vertebral arterial flow were compared with betahistine in anesthetized dogs. Pressure in the carotid artery was measured by a pressure transducer and mean arterial pressure was obtained by electrical integration. Heart rate was obtained by a cardiotachometer, triggered by a signal from the pressure pulse. The vertebral arterial flow was measured by fitting an electromagnetic flow transducer. The action on systemic mean arterial pressure, heart rate and vertebral arterial flow were represented by Δ mmHg, Δ beats/min and percent increase.

What is claimed is:

1. A compound of the formula:

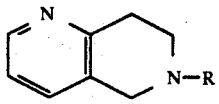

wherein R is $C_{5-7}$ alkyl or $C_{2-10}$ alkyl substituted by hydroxyl, lower alkylcarbonyl, lower alkyloxycarbonyl or phenoxy; $C_{2-10}$ unsaturated aliphatic hydrocarbon group having up to two unsaturated double bonds; phenyl-lower alkyl which is unsubstituted or substituted on the phenyl ring by halogen, lower alkyl, lower alkoxy, lower alkylene dioxy or lower alkylthio; cinnamyl which is unsubstituted or substituted on the phenyl ring by halogen, nitro, lower alkyl, lower alkoxy or lower alkylene dioxy; propargyl; 1-naphthylmethyl; 2-thenyl; cyclohexenyl; ($C_{3-6}$ cycloalkyl)-lower alkyl; 6-(5,6,7,8-tetrahydro-1,6-naphthyridino)-$C_{2-4}$ alkyl; 6-(5,6,7,8-tetrahydro-1,6-naphthyridino)-butenyl; or diphenylmethyl or a pharmaceutically acceptable salt thereof.

2. A compound of claim 1, wherein R is $C_{5-7}$ alkyl, allyl, 3-butenyl, 2-octenyl, cyclopropylmethyl, cyclobutylmethyl, 3-phenoxypropyl, benzyl, 4-methylbenzyl, 3-isopropylbenzyl, 4-isopropylbenzyl, 3,4-dichlorobenzyl, 3,4-dimethoxybenzyl, 3-n-propoxy-4-methoxybenzyl, 3,4-di-n-propoxybenzyl, 2-phenylethyl, 3-phenylpropylcinnamyl or 2,4-dichlorocinnamyl.

3. A compound of claim 2, wherein R is allyl, 3-butenyl, 2-octenyl, cyclopropylmethyl, 3-phenoxypropyl, 4-isopropylbenzyl, 3,4-dimethoxybenzyl or 2,4-dichlorocinnamyl.

4. A compound of claim 3, wherein R is allyl, cyclopropylmethyl, 3,4-dimethoxybenzyl or 2,4-dichlorocinnamyl.

5. A compound of claim 4 which is 5,6,7,8-tetrahydro-6-allyl-1,6-naphthyridine.

6. A compound of claim 4 which is 5,6,7,8-tetrahydro-6-cyclopropylmethyl-1,6-naphthyridine.

7. A compound of claim 4 which is 5,6,7,8-tetrahydro-6-(3,4-dimethoxybenzyl)-1,6-naphthyridine.

8. A compound of claim 4 which is 5,6,7,8-tetrahydro-6-(2,4-dichlorocinnamyl)-1,6-naphthyridine.

9. A composition for inhibiting vertigo or improving the cerebral circulation in dosage unit form which comprises 1 to 99% by weight of a compound of claim 1 or a pharmaceutically acceptable salt thereof in a dosage effective for inhibiting vertigo or improving cerebral circulation and 99 to 1% by weight of a medicinal adjuvant therefor.

10. a composition of claim 9 wherein said dosage unit form is a tablet.

11. A method of inhibiting vertigo in a patient which comprises administering to said patient an amount effective to inhibit vertigo in said patient of a compound of claim 1, 2, 3, 4, 5, 6, 7, 8.

12. A method of improving circulation in a patient which comprises administering to said patient an amount effective to improve the cerebral circulation of said patient of a compound of claim 1, 2, 3, 4, 5, 6, 7 or 8.